United States Patent [19]

Gordon et al.

[11] 4,042,639

[45] Aug. 16, 1977

[54] OXYCHLORINATION PROCESS

[75] Inventors: Theodore H. Gordon; Herman Fred Kummerle, both of Toledo, Ohio

[73] Assignee: Owens-Illinois, Inc., Toledo, Ohio

[21] Appl. No.: 525,550

[22] Filed: Nov. 20, 1974

Related U.S. Application Data

[63] Continuation of Ser. No. 703,301, Feb. 6, 1968, abandoned.

[51] Int. Cl.$^2$ ............................................. C07C 21/02
[52] U.S. Cl. ................................ 260/656 R; 423/488
[58] Field of Search ........... 260/656 R, 652 P, 654 A, 260/654 S; 423/488

[56] References Cited

U.S. PATENT DOCUMENTS

| | | | |
|---|---|---|---|
| 3,233,978 | 2/1966 | Alkemade | 423/488 |
| 3,551,506 | 12/1970 | Weinstein | 260/656 R |
| 3,816,599 | 6/1974 | Kafes | 423/488 |

*Primary Examiner*—Delbert E. Gantz
*Assistant Examiner*—Joseph A. Boska
*Attorney, Agent, or Firm*—Charles S. Lynch

[57] ABSTRACT

Contacting the vapor product of an ethane oxychlorination reaction with relatively cold, liquid, aqueous hydrogen chloride to produce an absorbate containing substantial amounts of inorganic constituents, including hydrogen chloride and water, that were in the vapor product. At least a portion of the absorbate is then distilled at a first pressure, usually above atmospheric pressure, to produce an overhead, usually hydrogen chloride, and aqueous hydrogen chloride bottoms which are usually of substantially azeotropic concentration at the first pressure. These bottoms are then distilled at a second pressure, usually atmospheric pressure, to produce an overhead, usually water, and bottoms of aqueous hydrogen chloride, usually of substantially azeotropic concentration at the second pressure.

2 Claims, 2 Drawing Figures

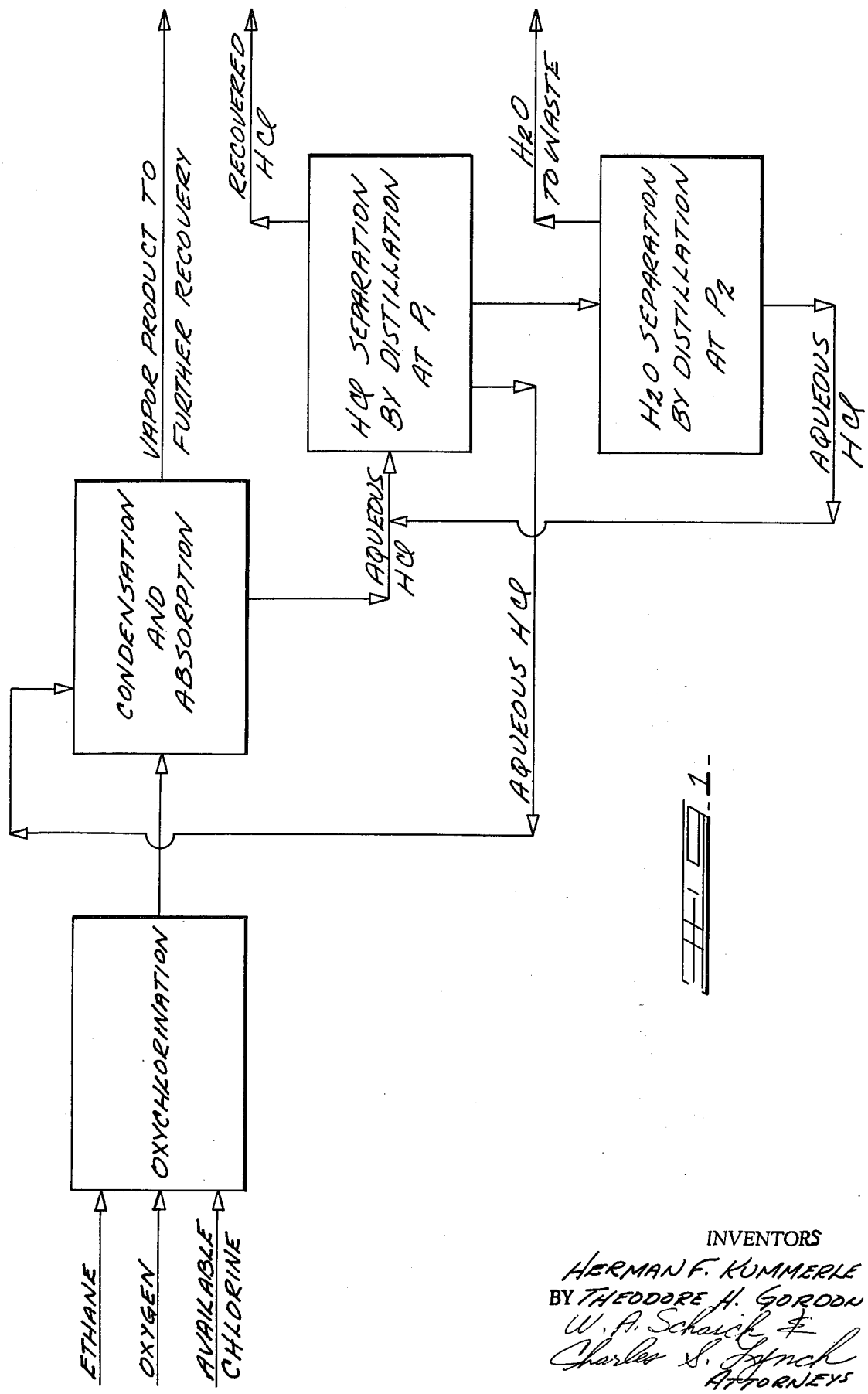

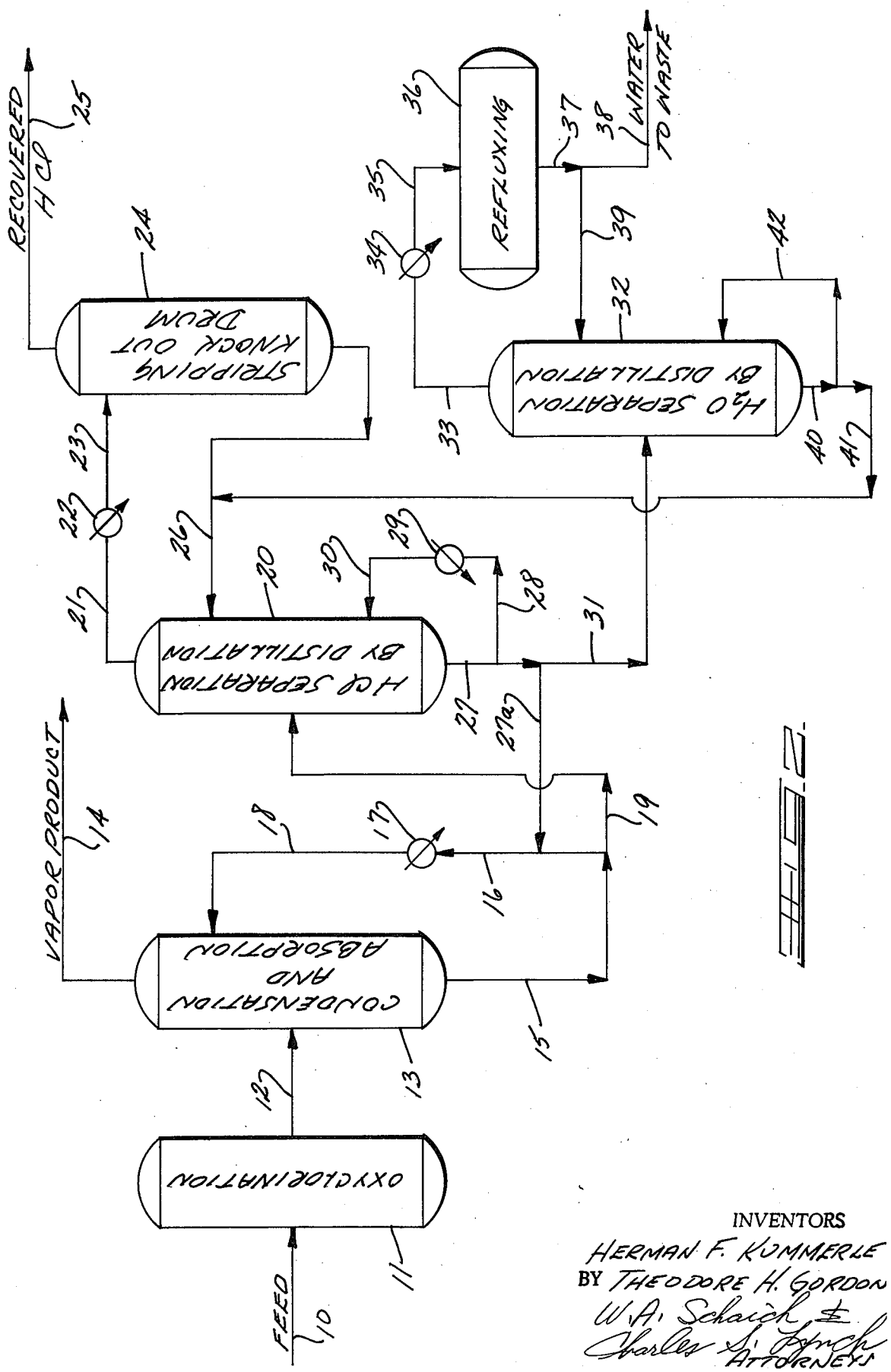

ically between the components of the product, particularly between the desired organic products and certain of the inorganic constituents.
OXYCHLORINATION PROCESS This is a continuation, of application Ser. No. 703,301, filed Feb. 6, 1968, now abandoned, which is relied upon and the entire disclosure and specification of which is hereby incorporated by reference.

DISCLOSURE OF THE INVENTION

This invention relates to the oxychlorination of ethane to produce vinyl chloride and more especially, to improved methods for purifying the product resulting from such oxychlorination.

Oxychlorination of ethane to produce vinyl chloride can generally be described as the reaction between available chlorine, ethane and oxygen at an elevated temperature in the presence of a multivalent metal compound catalyst.

As used in the specification and the appended claims, available chlorine is the chlorine in the elemental chlorine charged, in the hydrogen chloride charged, and one-half the chlorine present in 1,1-dichloroethane and 1,2-dichloroethane charged to the reaction zone, should these be present in the feed. If ethyl chloride is present in the feed, none of the chlorine present in ethyl chloride is considered available.

Many catalysts have been proposed for this reaction, including compounds of iron, copper, cerium, manganese, uranium, vanadium, nickel, chromium, cobalt, as well as other Group IVb, Vb, VIb, VIIb, VIII, IVa, Va and VIa metals or combinations thereof. Certain inorganic compounds of lithium, sodium potassium, rubidium, boron, indium, phosphorus, and thallium, act as promoters in combination with the catalyst ingredients listed above. The catalysts can be used in a fixed, fluid or suspended bed form, and can include a support such as diatomaceous earth, quartz, Vycor (96% silica glass), alumina, pumice, silica gel, mullite, Kieselguhr, etc.

Such oxychlorination of ethane produces vinyl chloride, ethylene, water and hydrogen chloride admixed with side products or other materials, such as unreacted feed materials. Difficulties have been encountered in resolving the vapor product of this process due to chemical interaction between the components of the product, particularly between the desired organic products and certain of the inorganic constituents.

Because substantial amounts of hydrogen chloride are present in the reaction product resulting from the oxychlorination of ethane with available chlorine, a method for recovering hydrogen chloride from the vapor product for recycle to the reaction is necessary if the process is to be economically attractive. Difficulties have been encountered in separating hydrogen chloride from the water in the vapor product because these components form an azeotropic mixture.

It has been found that inorganic constituents, including hydrogen chloride and water, can be removed from the vapor product of an ethane oxychlorination by intimately contacting the vapor product with relatively cold, liquid, aqueous hydrogen chloride. By relatively cold is meant that the aqueous hydrogen chloride is at a temperature below the temperature of the vapor product contacted therewith. Usually, the relatively cold, liquid, aqueous hydrogen chloride is at a temperature of about $-25°$ to $212°$ F., more usually about $30°$ to $150°$ F., and has a hydrogen chloride concentration of about 13 to 50 weight percent. Such treatment of the vapor product removes substantial quantities of the water and hydrogen chloride from the vapor product, while vinyl chloride, ethylene, other hydrocarbons and chlorinated hydrocarbons, as well as any carbon monoxide and carbon dioxide formed during the oxychlorination reaction, remain in the vapor phase and can be further resolved by suitable techniques. Additionally, entrained catalyst present in the vapor product is removed from the vapor product during the contacting step and can be recovered from the aqueous hydrogen chloride absorbate by suitable techniques, such as filtration.

Recovery of hydrogen chloride from the aqueous hydrogen chloride absorbate cannot be accomplished by simple distillation since hydrogen chloride and water form an azeotropic mixture. One technique which has been proposed for separating hydrogen chloride from water in the absorbate is distillation of the absorbate to recover a hydrogen chloride distillate stream therefrom and to produce a distilland which is an azeotropic mixture of hydrogen chloride and water. A reagent which eliminates the azeotrope-forming property of the distilland is added to break the azeotrope and the mixture of water, hydrogen chloride, and the reagent is distilled to recover more hydrogen chloride therefrom. In such a process, it is necessary to separate the resulting mixture of water and the reagent in order to regenerate the reagent for recycle and breaking of further quantities of azeotrope. While this process is satisfactory, it would be desirable to eliminate the need for using a reagent, which must be discarded or regenerated, to break the azeotrope and permit full hydrogen chloride recovery.

Accordingly, it is an object of this invention to provide an improved process for producing vinyl chloride by the oxychlorination of ethane.

Another object of this invention is to provide an improved process for the resolution of the vapor product of an oxychlorination reaction.

Still another object of the invention is to provide a process for the removal of inorganic constituents, including water and hydrogen chloride, from the vapor product of an ethane oxychlorination reaction and for resolution of the water and hydrogen chloride without the necessity of utilizing an added reagent to eliminate the azeotrope-forming property of water-hydrogen chloride mixtures.

According to one embodiment of this invention, there is provided a process for removal of inorganic constituents, including hydrogen chloride and water, from the vapor product of a catalytic ethane oxychlorination reaction with oxygen and available chlorine which comprises intimately contacting the vapor product with relatively cold, liquid, aqueous hydrogen chloride to remove inorganic constituents, including hydrogen chloride and water, from the vapor product. Such contacting condenses and absorbs water and hydrogen chloride from the vapor product thereby forming a resulting absorbate and a vapor stream containing vinyl chloride and ethylene. At least a portion of the resulting absorbate is distilled at a first pressure to form an overhead and bottoms of aqueous hydrogen chloride of substantially azeotropic composition at the pressure of the distillation. When the absorbate has a hydrogen chloride concentration above azeotropic concentration at the first pressure, the overhead in the distillation will be hydrogen chloride. However, when the hydrogen chloride concentration of the absorbate is below azeotropic concentration at the first pressure, the overhead will be water. At least a portion of the bottoms from the first distillation is distilled at a second pressure to recover an overhead of hydrogen chloride or water, whichever was not produced in the first distillation, and a second stream of aqueous hydrogen chloride bottoms of substantially azeotropic concentration at the second pressure.

According to another and more specific embodiment of this invention, there is provided a process wherein the absorbate has a hydrogen chloride concentration greater than the azeotropic concentration at atmospheric pressure, and which includes distilling at least a portion of the absorbate at a first pressure which is greater than atmospheric pressure to form an overhead of hydrogen chloride and a first stream of aqueous hydrogen chloride bottoms of substantially azeotropic concentration at the first pressure. At least a portion of the first stream of aqueous hydrogen chloride bottoms is then distilled at a second pressure which is less than the first pressure to form an overhead of water and a second stream of aqueous hydrogen chloride bottoms of substantially azeotropic concentration at the second pressure. The second stream of aqueous hydrogen chloride bottoms can then be distilled at the first pressure, usually by recycling the stream to the distillation at the first pressure, to form further overhead of hydrogen chloride and a further stream of aqueous hydrogen chloride bottoms of substantially azeotropic concentration at the first pressure. A portion of the first stream of aqueous hydrogen chloride bottoms can be, and usually is, recycled to the contacting step to condense and absorb further quantities of inorganic constituents from the oxychlorination vapor product.

Other objects, features and advantages of this invention will be apparent to those skilled in the art from the following detailed description of the invention and the drawings, wherein FIG. 1 is a flow diagram of one embodiment of this invention; and FIG. 2 is a schematic representation of a process in accordance with one embodiment of this invention.

As illustrated in FIG. 1, ethane, oxygen and available chlorine are reacted at an elevated temperature in the vapor phase in the presence of an oxychlorination catalyst to yield a vapor product stream containing vinyl chloride, ethylene, water and hydrogen chloride. The vapor product stream is then intimately contacted with relatively cold, liquid, aqueous hydrogen chloride in the condensation and absorption step. In this manner, there is formed an absorbate containing substantial amounts of the hydrogen chloride and water from the vapor product stream, along with an overhead containing the vinyl chloride, ethylene and other organic products of the oxychlorination reaction.

To recover hydrogen chloride and water from the absorbate, this invention makes use of the principle that the composition of an azeotrope is changed when the total system pressure is varied. Based on this principle, the water and hydrogen chloride in the absorbate are separated in two distillation steps at different pressures. The water-hydrogen chloride azeotrope has a composition of approximately 20.2 weight percent hydrogen chloride at atmospheric pressure. At higher pressures, the weight percent of hydrogen chloride in the azeotrope is less than 20 weight percent. For example, at 55 psig, the water-hydrogen chloride azeotrope contains 17.5 weight percent hydrogen chloride. The concentration of this azeotrope at other pressures has been reported in the literature and is known to those skilled in the art.

In accordance with this invention, the water and hydrogen chloride in the absorbate are separated by distillation in two steps, at different pressures. Depending on its concentration, the absorbate is first distilled at either subatmospheric pressure, atmospheric pressure or elevated pessure, as will be explained below. Since the absorbate obtained normally has a hydrogen chloride concentration greater than the azeotropic concentration at atmospheric pressure, the first distillation usually takes place at above atmospheric pressure. This is illustrated in FIG. 1.

As illustrated in FIG. 1, after the absorption and condensation step, the aqueous hydrogen chloride absorbate is withdrawn and distilled at a first pressure $P_1$, which is above atmospheric pressure, to recover a hydrogen chloride stream therefrom as overhead. The overhead from the first distillation can be as pure hydrogen chloride as required. Bottoms from the first distillation step, which are an aqueous hydrogen chloride stream having a hydrogen chloride concentration of substantially azeotropic concentration at the pressure of the first distillation (usually slightly higher than the azeotropic concentration at the first pressure) are fed to the second distillation step which is performed at a second pressure $P_2$, lower than the first pressure.

In the lower pressure distillation, which is usually at atmospheric pressure, the overhead is essentially pure water and the bottoms are an aqueous hydrogen chloride stream in which the hydrogen chloride concentration is substantially the azeotropic concentration at the second pressure (usually slightly lower than the azeotropic concentration at the second pressure); bottoms from this second distillation step are recycled as a second feed stream to the first distillation step.

In order to provide a continuous source of quenching solution, a portion of the bottoms from the higher pressure distillation step is recycled to the condensation and absorption step for treatment of further quantities of oxychlorination vapor product.

Hydrogen chloride recovered from the vapor product by the process of this invention is preferably recycled to the ethane oxychlorination to serve as at least a part of the available chlorine, thereby minimizing the amount of the available chlorine consumed in the ethane oxychlorination reaction of this invention. While a nearly anhydrous hydrogen chloride overhead is usually recovered in the distillation, it is feasible to recover, as the overhead from the higher pressure distillation, a stream of hydrogen chloride containing substantial quantities of water.

Those skilled in the art will appreciate that when the absorbate has a hydrogen chloride concentration less than the azeotropic concentration at atmospheric pressure, the initial distillation will be performed at atmospheric pressure to recover overhead of a nearly-pure water stream; the bottoms, which are an aqueous hydrogen chloride stream of substantially azeotropic concentration at atmospheric pressure, will be distilled at elevated pressure to recover hydrogen chloride overhead therefrom and form bottoms having a hydrogen chloride concentration of substantially the azeotropic concentration at the pressure of the second distillation. These bottoms from the higher pressure distillation can be recycled to the distillation at atmospheric pressure and thus the overall process will be similar to the process illustrated in FIG. 1.

While the preceding has stated that the aqueous hydrogen chloride absorbate is distilled at the first pressure to recover an overhead therefrom and form an azeotrope of water and hydrogen chloride, it is unnecessary to distill the absorbate down to azeotropic concentration. Rather, the aqueous hydrogen chloride absorbate can be distilled to any convenient hydrogen chloride concentration with the azeotropic concentration at the pressure employed being a limit of hydrogen chloride concentration in the solution resulting from the distillation. The aqueous hydrogen chloride bottoms resulting from the distillation at the first pressure can then be distilled at the second pressure with the azeotropic concentration at the second pressure being a limit of hydrogen chloride concentration in the bottoms from this distillation.

In the distillations, pressure conditions are selected so that the desired overhead is obtained. To obtain hydrogen chloride overhead, the pressure chosen is one at which the aqueous hydrogen chloride stream being distilled has a hydrogen chloride concentration greater than azeotropic concentration. To obtain water overhead, the pressure selected is one at which the aqueous hydrogen chloride stream being distilled has a hydrogen chloride concentration less than azeotropic concentration. For convenience and to obtain good separation in each step, one distillation usually is conducted at elevated pressure (for example 55 psig) and the other at atmospheric pressure. However, it will be understood that both distillations can be conducted at elevated pressure as long as one pressure is higher than the other. Also, one distillation can be conducted at subatmospheric pressure and the other at a different pressure which is subatmospheric, atmospheric or above atmospheric pressure. Since the concentration of the azeotrope varies with pressure, the percentage of the aqueous hydrogen chloride stream being distilled which can be recovered as hydrogen chloride or water overhead in each step depends on the pressure conditions used.

After being freed from substantial amounts of water and hydrogen chloride in accordance with this invention, the vapor product can be further resolved by suitable methods. Residual hydrogen chloride can be removed by water washing and residual water by scrubbing the vapor product with sulphuric acid. The vapor stream can then be treated in an absorber with a suitable solvent for the separation of chlorinated hydrocarbons from the remainder of the vapors. Dichloroethane, trichloroethane, tetrachloroethane and other selective solvents are suitable. The chlorinated products can be recovered from the solvent by stripping, and the chlorinated products separated and purified in a series of distillation towers. After removal of the chlorinated hydrocarbons, ethylene can be removed and recovered from the vapor product stream in accordance with known techniques, or can be converted to ethyl chloride, ethylene dichloride, etc., as desired.

The following example, using the system illustrated in FIG. 2, exemplifies a continuous oxychlorination process in accordance with the present invention, but it is not intended that the invention be limited thereby. All parts set forth in the example are in pounds per hour.

EXAMPLE

With reference to FIG. 2, a feed stream having the composition set forth in Table I is fed through conduit 10 to fixed bed vapor phase oxychlorination reactor 11 which is maintained at a temperature of 1030° F. and a pressure of 50 psig. The catalyst is iron oxide-lithium oxide, 10% actives on −20 mesh fused Alundum, with the iron oxide to lithium oxide mole ratio being 3.6. Contact time if 0.48 seconds. The vapor product discharged through conduit 12 is at a temperature of 1022° F. and has the composition shown in Table II.

TABLE I.

| Material | Pounds per hour |
| --- | --- |
| $C_2H_6$ | 55,600 |
| $Cl_2$ | 30,800 |
| $N_2$ | 202,000 |
| $O_2$ | 61,400 |
| HCl | 186,000 |
| $H_2O$ | 6,800 |

TABLE II

| Material | Pounds per hour |
| --- | --- |
| $C_2H_3Cl$ | 50,800 |
| $C_2H_4$ | 22,700 |
| $C_2H_5Cl$ | 3,300 |
| HCl | 187,200 |
| $H_2O$ | 51,900 |
| Inerts* | 226,700 |

*Includes $N_2$, $C_2H_6$, $CH_4$, $C_2H_2$, $CH_3Cl$, $CO_2$, CO, etc.

Vapor product from oxychlorination reactor 11, at a pressure of 50 psig and a temperature of 1022° F., is passed through conduit 12 to scrubber 13 where the vapor product is scrubbed and quenched with aqueous hydrogen chloride at a temperature of 86° F. Quenching and scrubbing in scrubber 13 reduces the hydrogen chloride content of the vapor product from 187,200 parts of 520 parts, the water content from 51,900 parts to 4772 parts, and the temperature to 140° F. Vapor product is discharged from scrubber 13 through conduit 14.

During the quenching and scrubbing of the vapor product in scrubber 13, the temperature of the aqueous hydrogen chloride in scrubber 13 is increased to 243° F. To cool the aqueous hydrogen chloride and recover hydrogen chloride absorbed from the vapor product, an aqueous hydrogen chloride stream is withdrawn from scrubber 13 through conduit 15. The withdrawn aqueous hydrogen chloride stream is divided and a stream containing 160,022 parts hydrogen chloride and 468,871 parts water is conveyed through conduit 16 to heat exchanger 17 where the stream is cooled to 86° F. Cooled aqueous hydrogen chloride from heat exchanger 17 is recycled to scrubber 13 through conduit 18.

The remainder of the withdrawn aqueous hydrogen chloride stream, containing 496,312 parts hydrogen chloride and 1,457,672 parts water, is conveyed through conduit 19 to distillation tower 20. In distillation tower 20, the aqueous hydrogen chloride stream is distilled at a pressure of 55 psig to produce an overhead at a temperature of 291° F. containing 471,600 parts hydrogen chloride and 385,854 parts water. This overhead is conveyed through conduit 21 to heat exchanger 22 where its temperature is lowered to 131° F. From heat exchanger 22, the aqueous hydrogen chloride overhead is conveyed through conduit 23 to stripper knock-out drum 24 where vapor and liquid fractions are separated. The vapor fraction containing 186,680 parts hydrogen chloride and 374 parts water is conveyed through conduit 25 to storage or recycle to oxychlorination reactor 11. The liquid fraction from stripper knock-out drum 24, which contains 284,920 parts hydrogen chloride and 385,480 parts water, is recycled to the top of distillation tower 20 through conduit 26.

Bottoms from distillation tower 20 are an aqueous hydrogen chloride stream having a hydrogen chloride concentration of 18 weight percent; the azeotropic concentration at 55 psig is 17.5 weight percent hydrogen chloride. These bottoms are withdrawn from distillation tower 20 through conduit 27 and divided into three streams. A first stream is conveyed through conduit 28, heated in heat exchanger 29, and recycled to distillation tower 20 through conduit 30. A second stream of bottoms from distillation tower 20 containing 309,632 parts hydrogen chloride and 1,410,544 parts water is conveyed through conduit 27a to conduit 16 and into heat exchanger 17 where its temperature is lowered to 86° F. From heat exchanger 17, this stream is conveyed through conduit 18 to scrubber 13 where the stream is used to quench and scrub further quantities of vapor product.

A third stream of the bottoms from distillation tower 20, containing 84,157 parts hydrogen chloride and 383,383 parts water at a temperature of 306° F. is conveyed through conduits 27 and 31 to distillation tower 32. In distillation tower 32, the aqueous hydrogen chloride stream is distilled at atmospheric pressure to produce an overhead of 112,210 parts of water at 212° F. This overhead is conveyed through conduit 33 to heat exchanger 34 where it is cooled to 180° F. From heat exchanger 34, the water overhead is passed through conduit 35, refluxed in refluxing drum 36, and divided in conduit 37. 46,754 parts of the water in conduit 37 are conveyed through conduit 38 to disposal. The remainder of the water, 65,456 parts, is returned through conduit 39 as reflux to distillation tower 32.

Bottoms from distillation tower 32 are an aqueous hydrogen chloride stream having a concentration of 20 weight percent which is substantially the concentration of the atmospheric pressure azeotrope. These bottoms from distillation tower 32 are withdrawn through conduit 40 and divided. A stream containing 84,157 parts hydrogen chloride and 336,629 parts water is conveyed through conduit 41 to conduit 26 and discharged into distillation tower 20 where it is distilled at a pressure of 55 psig to recover hydrogen chloride therefrom. The remainder of the bottoms from distillation tower 32 is recycled to distillation tower 32 through conduit 42.

Thus, in the foregoing example, 186,680 pounds per hour of hydrogen chloride are removed from the ethane oxychlorination vapor product and recovered as a 99.8 weight percent hydrogen chloride stream suitable for recycle to the ethane oxychlorination reaction. Further, 47,128 pounds per hour of water are removed from the vapor product, with 46,754 pounds per hour of water being separated from the recovery system for disposal; 374 pounds per hour of water are removed from the recovery system as part of the aforesaid 99.8 weight percent hydrogen chloride stream.

As will be apparent to those of ordinary skill in the art, the vapor product leaving scrubber 13 through conduit 14 can be further resolved using known techniques. Residual hydrogen chloride can be removed by water washing or extraction with a suitable solvent, such as sulphuric acid, while residual water can be removed by scrubbing with sulphuric acid. The vinyl chloride and ethylene in the vapor product can be isolated from the system while the ethyl chloride can be recycled to the oxychlorination reaction or recovered as a product.

As shown by the above example, the present invention provides a continuous process for the oxychlorination of ethane. Hydrogen chloride produced in this reaction is separated from the vapor product substantially isolated from water, and can be recycled to serve as available chlorine in the oxychlorination reaction.

When practicing the process of this invention, there is substantially no net loss of hydrogen chloride since the hydrogen chloride produced by the oxychlorination reaction can be recycled to the reactor thereby minimizing the amount of make up available chlorine which must be used. Additionally, this process provides for the separation of the water produced by the oxychlorination reaction from the other products and for the elimination of this water from the system. In a continuous manner, this invention further provides for resolution of the water-hydrogen chloride azeotrope without the necessity of adding reagents to the system. This is a substantial advantage since possible contamination of the hydrogen chloride is thereby avoided and there is no added reagent to be regenerated. Further, a continuous source of quenching solution is also provided.

While the invention has been shown and described and illustrated with reference to certain preferred embodiments thereof, those skilled in the art will appreciate that various modifications, changes, and omissions can be made without departing from the spirit of the invention. Therefore, it is intended that the invention be limited only by the scope of the claims which follow.

What is claimed is:

1. In the process for the vapor phase oxychlorination of ethane with oxygen and available chlorine at elevated temperatures in the presence of a catalyst comprising at least one compound of a multivalent metal to produce a vapor product comprising vinyl chloride, ethylene, hydrogen chloride and water which entrains some catalyst; the improvement which comprises condensing and absorbing from said vapor product inorganic constituents comprising said catalyst, hydrogen chloride and water, by intimately contacting said vapor product with a relatively cold, liquid, aqueous hydrogen chloride stream to form a resulting absorbate having a hydrogen chloride concentration greater than the azeotropic concentration at atmospheric pressure and a vapor stream containing vinyl chloride and ethylene and being substantially free of entrained catalyst, distilling at least a portion of said absorbate at a first pressure greater than atmospheric pressure to form an overhead of hydrogen chloride and a first stream of aqueous hydrogen chloride bottoms at substantially azeotropic concentration at said first pressure, recycling a first portion of said first stream of aqueous hydrogen chloride bottoms to said contacting step, distilling a second portion of said first stream of aqueous hydrogen chloride bottoms at a second pressure which is atmospheric pressure to form an overhead of water and a second stream of aqueous hydrogen chloride bottoms of substantially azeotropic concentration at said second pressure and recycling said second stream of aqueous hydrogen chloride bottoms to said distillation at said first pressure.

2. In the process for the vapor phase oxychlorination of ethane with oxygen and available chlorine at elevated temperatures in the presence of a catalyst comprising at least one compound of a multivalent metal to produce a vapor product comprising vinyl chloride, ethylene, hydrogen chloride and water which entrains some catalyst; the improvement which comprises condensing and absorbing from said vapor product inorganic constituents comprising said catalyst, hydrogen chloride and water, by intimately contacting said vapor product with a relatively cold, liquid, aqueous hydrogen chloride stream to form a resulting absorbate having a hydrogen chloride concentration greater than the azeotropic concentration at atmospheric pressure and a vapor stream containing vinyl chloride and ethylene and being substantially free of entrained catalyst, distilling at least a portion of said absorbate at a first pressure greater than atmospheric pressure to form an overhead of hydrogen chloride and a first stream of aqueous hydrogen chloride bottoms at substantially azeotropic concentration at said first pressure, recycling a first portion of said first stream of aqueous hydrogen chloride bottoms to said contacting step, distilling a second portion of said first stream of aqueous hydrogen chloride bottoms at a second pressure which is less than said first pressure but not less than atmospheric pressure to form an overhead of water and a second stream of aqueous hydrogen chloride bottoms of substantially azeotropic concentration at said second pressure and recycling said second stream of aqueous hydrogen chloride bottoms to said distillation at said first pressure.

* * * * *